United States Patent
Allen et al.

(10) Patent No.: US 6,565,549 B1
(45) Date of Patent: May 20, 2003

(54) ABSORBENT ARTICLE WITH THERMALLY ACTIVATABLE ADHESIVES

(75) Inventors: Patrick J. Allen, Cincinnati, OH (US); Donald C. Roe, West Chester, OH (US); Mark J. Kline, Cincinnati, OH (US); Namy M. King, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/504,485

(22) Filed: Feb. 15, 2000

(51) Int. Cl.⁷ ............................................. A61F 13/15
(52) U.S. Cl. ............................... 604/385.04; 604/389
(58) Field of Search ............................... 604/365, 367, 604/383, 385.01, 385.03, 385.04, 385.14, 385.24, 385.29, 389–391

(56) References Cited

U.S. PATENT DOCUMENTS

| | | | |
|---|---|---|---|
| 3,777,759 A | 12/1973 | Oehmke et al. | 128/287 |
| 4,044,769 A | * 8/1977 | Mesek | 128/287 |
| 4,199,646 A | 4/1980 | Hori et al. | 428/344 |
| 4,699,146 A | 10/1987 | Sieverding | 128/640 |
| 4,846,828 A | 7/1989 | Mendelsohn | |
| 5,156,911 A | 10/1992 | Stewart | 428/355 |
| 5,387,450 A | * 2/1995 | Stewart | 428/40 |
| 5,589,246 A | 12/1996 | Calhoun et al. | 428/120 |
| 5,633,010 A | 5/1997 | Chen | 424/448 |
| 5,648,167 A | 7/1997 | Peck | 428/355 |
| 5,782,787 A | 7/1998 | Webster | 602/46 |
| 5,876,745 A | 3/1999 | Muraoka et al. | 424/448 |
| 5,889,118 A | 3/1999 | Delgado et al. | 525/228 |
| 5,921,977 A | * 7/1999 | Schmitz | 604/391 |
| 6,160,200 A | * 12/2000 | Ehrnsperger et al. | 604/378 |
| 6,166,285 A | * 12/2000 | Schulte et al. | 604/364 |
| 6,168,583 B1 | * 1/2001 | Tanji et al. | 604/385.14 |

FOREIGN PATENT DOCUMENTS

| | | | |
|---|---|---|---|
| EP | 1 016 392 A1 | 7/2000 | |
| WO | WO 95/05934 | 3/1995 | ........... B29C/65/50 |
| WO | WO 97/12561 A2 | 4/1997 | |
| WO | WO 98/10728 A1 | 3/1998 | |
| WO | WO 98/29517 | 7/1998 | .......... C09J/129/10 |
| WO | WO 98/58035 | 12/1998 | .......... C09J/153/02 |
| WO | WO 99/63018 | 12/1999 | ............. C09J/7/02 |
| WO | WO 00/00123 | * 1/2000 | ........... A61F/13/15 |
| WO | WO 00/38748 | 7/2000 | ........... A61L/15/58 |
| WO | WO 00/59427 A1 | 10/2000 | |

* cited by examiner

*Primary Examiner*—Weilun Lo
*Assistant Examiner*—Jamisue A. Webb
(74) *Attorney, Agent, or Firm*—Ian S. Robinson; David M. Weirich; Ken K. Patel

(57) ABSTRACT

An absorbent article comprising a topsheet, a backsheet joined with at least a portion of the topsheet, an absorbent core disposed between at least a portion of the topsheet and the backsheet; and a thermally activatable adhesive capable of adhering of the absorbent article to the skin of the wearer during use. The thermally activatable adhesive is preferably activated at temperatures in the range of about 30° C. to about 60° C.

60 Claims, 7 Drawing Sheets

ABSORBENT ARTICLE WITH THERMALLY ACTIVATABLE ADHESIVES

FIELD OF THE INVENTION

This invention is directed to hygienic absorbent articles, such as diapers, adult incontinence articles, feminine protection articles and the like. More particularly, the invention relates to absorbent articles including thermally activatable adhesives.

BACKGROUND OF THE INVENTION

Absorbent articles are well known in the art. These articles typically have an absorbent core, which is held or positioned against the body of the wearer during use by a fastening system, such that the bodily exudates are caught by the article. Typical absorbent articles include a topsheet facing the wearer which permits fluid exudates to pass through and a backsheet which prevents the exudates from escaping from the absorbent article.

Many advancements have been made in the art since the introduction of the disposable absorbent article. However, problems still exist relating to isolation of bodily waste, such as fecal material, and application of the article to the wearer. Attempts have been made to isolate fecal waste by employing pockets, topsheets with receiving apertures, spacing elements, barrier cuffs, and other physical means. These generally have the deficiency of inadequately maintaining coordination with the wearer's body, especially the waste outlet points and/or the portions of the wearer's body near the perimeter of the product. Attempts have also been made to improve the application of the article to the wearer by the use of adhesive tapes and mechanical fastening systems such as Velcro®. However, the articles are still difficult to apply to mobile wearers using only two hands.

In an effort to overcome the deficiencies of the prior art, topical adhesives such as hydrocolloid, silicone, and hydrogel adhesives have been incorporated into disposable articles as a means of better positioning the article or maintaining body contact. However, these attempts fail to provide an adequately convenient means of using the product because they require release paper to prevent accidental contamination of the adhesive during manufacture, storage, and preparation. Additionally, such embodiments may result in inadvertent sticking of the article to the caregiver's hands and/or the wearer's clothing, legs, etc. (e.g., regions of the body outside the intended attachment area).

Thus, it would be desirable to provide absorbent articles with improved fit and sealing which can be sustained during use. It would also be desirable to provide an article which maintains coordination with a specific area of the wearer's anatomy. Further, it would be advantageous to provide an article with a thermally activatable topical adhesive which helps maintain the article in the desired configuration or location without irritating or harming the wearer's skin. Even further, it would be advantageous to provide an article having a topical adhesive which is thermally activatable during the course of applying or wearing the article.

SUMMARY OF THE INVENTION

The present invention solves the deficiencies of the prior art by providing an absorbent article comprising a topsheet, a backsheet joined with at least a portion of the topsheet, an absorbent core disposed between at least a portion of the topsheet and the backsheet, and a thermally activatable adhesive disposed on at least a portion of the article. The thermally activatable adhesive is preferably capable of adhering the absorbent article to the skin of the wearer during at least a portion of the product's use or a portion of the absorbent article to itself during use. Further, the thermally activatable adhesive is activated by the wearer or caregiver or when a certain condition is met within the article to facilitate easy and comfortable removal of the product from the wearer or to facilitate comfortable wearing of the product. For example, the thermally activatable adhesive may be activated at temperatures in the range of about 28° C. to about 60° C.

BRIEF DESCRIPTION OF THE DRAWINGS

FIG. 2A is a plan view of an alternative embodiment of the disposable diaper configuration of the present invention.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, wipes, mops, bandages and the like.

Figure 1:
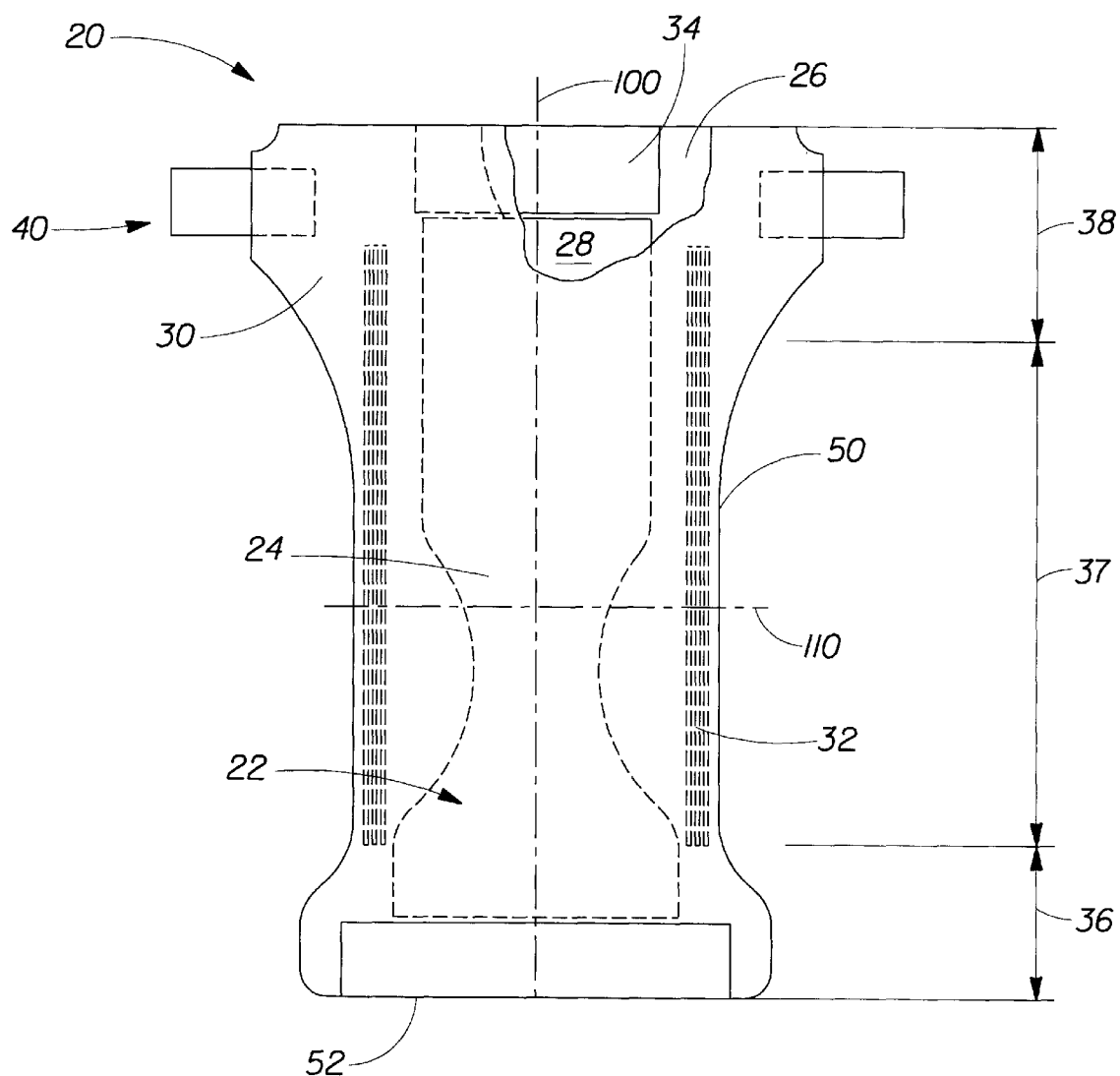
FIG. 1 is a plan view of a disposable diaper embodiment of the present invention with portions cut away to reveal underlying structure.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 is shown in FIG. 1 to have a first waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The backsheet 26 is generally that portion of the diaper 20 positioned adjacent the garment facing surface of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by EXXON Chemical Co., of Bay City, Tex., under the designation EXXAIRE and monolithic films such as manufactured by Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. Pat. No. 5,938,648 issued to LaVon on Aug. 17, 1999, U.S. Pat. No. 5,865,823 issued to Curro on Feb. 2, 1999 and U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body facing surface of the absorbent core 28 and may be partially or wholly joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 may comprise one or more apertures 80 to ease penetration of exudates therethrough, such as urine and/or feces (solid, semi-solid, or liquid). The size of at least the primary aperture 80 is important in achieving the desired waste encapsulation performance. If the primary aperture 80 is too small, the waste may not pass through the aperture, either due to poor alignment of the waste source and the aperture location or due to fecal masses having a diameter greater than the aperture 80. If the aperture 80 is too large, the area of skin that may be contaminated by "rewet" from the article is increased. Typically, the aperture 80 should have an area of between about 10 cm$^2$ and about 50 cm$^2$. The aperture 80 preferably has an area of between about 15 cm$^2$ and 35 cm$^2$.

Further, the topsheet 24 may be fully or partially elasticated or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which are incorporated by reference herein.

The topsheet 24 is preferably compliant, soft feeling, and non-irritating to the wearer's skin. Further, at least a portion of the topsheet 24 is liquid pervious, permitting liquids to readily penetrate through its thickness. At least a portion of the topsheet 24 may be impermeable to liquids and solids or semi-solids or may be permeable to exudates only in a direction away from the wearer. Further, the topsheet 24 may include regions of differing permeability. For example, the topsheet 24 may be liquid permeable in the urine loading region of the diaper (generally front waist region and/or crotch region) and may be impermeable in other areas (e.g., in the area surrounding an aperture 80). Such configuration may provide good urine acquisition characteristics while preventing feces which pass through the aperture 80 from passing back towards the wearer's skin. The topsheet 24 may additionally comprise a multiplicity of secondary apertures as described in more detail in U.S. Pat. No. 5,342,338 issued to Roe on Aug. 30, 1994 entitled "Disposable Absorbent Article For Low-Viscosity Fecal Material". These secondary apertures generally each have an area which is less than the area of the primary aperture but provide a means for low viscosity bodily wastes to penetrate the topsheet 24 if the wastes contact the topsheet 24 in a region other than that of the primary aperture 80.

A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheet includes fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, at least a portion of the topsheet 24 is made of a hydrophobic material or is treated to be hydrophobic in order to isolate the wearer's skin from liquids contained in the absorbent core 28. If the topsheet 24 is made of a hydrophobic material, preferably at least a portion of the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein. Alternatively, the topsheet 24 may include an apertured web or film which is hydrophobic. This may be accomplished eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. Nos. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). Exemplary absorbent structures for use as the absorbent core are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The diaper 20 may also include a sublayer disposed between the topsheet 24 and the backsheet 26. The sublayer may be any material or structure capable of accepting, storing or immobilizing bodily exudates. Thus, the sublayer may include a single material or a number of materials operatively associated with each other. Further, the sublayer may be integral with another element of the diaper 20 or may be one or more separate elements joined directly or indirectly with one or more elements of the diaper 20. Further, the sublayer may include a structure that is separate from the core 28 or may include or be part of at least a portion of the core 28.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and more specifically, having pores greater than about 1.0 mm in diameter.) One embodiment of a storage element includes a mechanical fastening loop landing element, having an uncompressed thickness of about 1.5 millimeters available as XPL-7124 from is the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent storage elements are described in European Patent Application No. EP 0 847 738 A1 entitled "Disposable Absorbent Article Having Capacity to Store Low-Viscosity Fecal Material" published Jun. 17, 1998 in the name of Roe and U.S. Pat. No. 5,941,864 entitled "Disposable Absorbent Article Having Improved Fecal Storage" issued to Roe on Aug. 24, 199, both of which are hereby incorporated by reference herein. Further, the sublayer, or any portion thereof, may include or be coated with a lotion or other known substances to add, enhance or change the performance or other characteristics of the element.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. The fastening system 40 preferably maintains the first waist region 36 and the second waist region 38 in a configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151, 092 issued to Buell on Sep. 9, 1992; and U.S. Pat. No. 5,221,274 issued to Buell on Jun. 22, 1993. Another exemplary fastening system is disclosed in co-pending U.S. application Ser. No. 09/143,184 entitled "Absorbent Article Fastening Device" in the names of Kline et al. filed on Aug. 28, 1998. The fastening system may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 to reduce shifting of overlapped portions or to improve fit as disclosed in U.S. Pat. Nos. 5,242,436; 5,499,978; 5,507,736; 5,591,152. Each of these patents is incorporated herein by reference. In alternative embodiments, opposing sides of the garment may be seamed or welded to form a pant. This allows the article to be used as a pull-on diaper or training pant.

The diaper 20 may also comprise side panels 30. The side panels 30 may be elastic or extensible to provide a more comfortable and contouring fit. The diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5, 221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. Pat. No. 5,897,545 issued to Kline, et. al. on Apr. 27, 1999; U.S. Pat. No. 5,899,895 issued to Robles, et al. on May 4, 1999 entitled "Disposable Absorbent Article With Extensible Side Panels"; each of which is incorporated herein by reference.

The diaper 20 preferably further includes leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

Preferably, the diaper 20 includes a thermally activatable adhesive 90 which acts to hold the article or some portion thereof in place during use. For example, the longitudinal, lateral, and/or the z-directional placement (i.e. direction normal to the wearer)of the article may be maintained by the thermally activatable adhesive 90. Alternatively, the adhesive 90 may be used to adhere a portion of the article to another portion of the article or a different article. The thermally activatable adhesive may also be used as a disposal means for holding the article in a proper configuration for disposal after use.

A "thermally activatable" adhesive is an adhesive which exhibits an increase in "tack" or adhesion after being warmed to a temperature at or above the activation temperature of the adhesive. The "activation temperature" of a thermally activatable adhesive is the temperature at which a the adhesive is activated (i.e., the temperature at which the adhesion of the adhesive increases significantly, as described herein). In certain embodiments wherein the maximum adhesion is achieved over a range of temperatures, the activation temperature is the temperature at which the increase in adhesion begins. Preferably, the activation temperature of the thermally activatable adhesive is between about 28° C. and 60° C. More preferably, the activation temperature is between about 30° C. and 40° C. However, the activation temperature may be any temperature that may be reasonably experienced in the context of an absorbent article. However, in cases where the activatable adhesive is used, for example, only during application of the article and not expected to be active during the article's use, the adhesive preferably remains active between about 33° C. and about 60° C., more preferably between about 37° C. and about 49° C. and even more preferably between about 39° C. and about 45° C.

The activatable adhesive may also be thermally deactivatable and/or thermally reversible. A thermally deactivatable adhesive exhibits a decrease in "tack" or adhesion after being cooled to a temperature at or below the deactivation temperature of the adhesive. The "deactivation temperature" of a thermally deactivatable adhesive is the temperature at which the adhesive is deactivated (i.e., the temperature at which the adhesion of the adhesive decreases significantly, as described herein). A thermally reversible adhesive may be activated by an increase in temperature and, subsequently, deactivated by a corresponding decrease in temperature. The "deactivation temperature" of a thermally reversible adhesive is the temperature at which the adhesive is deactivated (i.e., the temperature at which the adhesion of the adhesive decreases significantly, as described herein). The activation temperature and deactivation temperature of thermally reversible adhesives may be the same or different temperatures.

Preferably, the adhesive force, or adhesion, of the thermally activatable adhesive is essentially zero prior to activation. In one preferred embodiment the pre-activation adhesion of the thermally activatable adhesive 90 is less than about 10 g/in as measured by the Adhesion Method described below. In another embodiment, the pre-activation adhesion is between about 2 g/in and about 100 g/in, and preferably between about 5 g/in and about 50 g/in. Once activated, the adhesive preferably has a sufficient adhesion to perform the intended function (for example, hold an article in contact with the skin). In certain embodiments of the present invention, the thermally activatable adhesive 90 may have an unactivated adhesion value measurably greater than zero. In these cases, the adhesive force of the thermally activatable adhesive 90 after activation is typically at least about twice that of the adhesive prior to activation. Preferably, the adhesive force of the thermally activatable adhesive 90 after activation is typically at least about three times that of the adhesive prior to activation. More preferably, the adhesive force of the thermally activatable adhesive 90 after activation is typically at least about five times that of the adhesive prior to activation. Even more preferably, the adhesive force of the thermally activatable adhesive 90 after activation is at least 10 times that of the adhesive prior to activation and may be at least about one hundred times that of the adhesive prior to activation. In one preferred embodiment, the post-activation adhesion of the thermally activatable adhesive is between about 25 g/in and about 700 g/in, and more preferably between about 50 g/in and 400 g/in.

The elapsed time required for activation of the thermally activatable adhesive 90 while in contact with the object having a temperature at or above the activation temperature is important to performance of the disposable absorbent article of the present invention. The activation should be rapid enough to reduce the likelihood that the product will shift on the wearer before the adhesive has time to activate which could lead to inadvertent adhesion of the article in an undesirable location on the wearer. On the other hand, the activation should be slow enough to prevent inadvertent adhesion of the product to the wearer's or caregiver's skin in an undesirable location during the application process and prior to final positioning of the product. Typically, in preferred adhesive embodiments described in more detail below, the elapsed time required for activation should be between about 2 seconds and about 30 seconds, and preferably between about 5 seconds and about 15 seconds. In any case, the time required for activation may be decreased by increasing the surface area-to-mass ratio of the adhesive (e.g., by decreasing the thickness of the adhesive layer or forming "strings" of the adhesive). Conversely, the time required for activation may be increased by decreasing the surface area-to-mass ratio of the adhesive.

The thermally activatable adhesive of the present invention may be a topical adhesive. A "topical adhesive", as used herein is defined as an adhesive formulated for use in direct skin contact, such as adhering a bandage or other article to the skin. Preferred embodiments of thermally activatable topical adhesives exhibit this increase in "tack" or adhesion upon sustained contact with the wearer's skin. The activation temperature of thermally activated topical adhesives activated by skin temperature will typically be between about 33° C. and 38° C., more preferably between about 35° C. and 37° C. Topical adhesives should be non-irritating and generally compatible with human skin. Further, the in-use tack or adhesion level should be sufficient so as to be able to maintain coordination with the wearer's anatomy, but not so aggressive so as to be unduly difficult or painful to remove from the skin.

In any configuration, the thermally activatable adhesive may be warmed (i.e., activated) via direct or indirect contact with an object or material (i.e., via conduction), such as the wearer's skin, having a temperature at or above the activation temperature of the adhesive. Alternatively, the adhesive may be warmed via a field (i.e., radiation) or convective current (such as air) from a non-contacting heat source. Other means for heating the adhesive include, but are not limited to exothermic chemical reaction such as the oxidation of iron filings, and creation of solutions having positive heats of solution (i.e., release heat upon formation of a solution) such as the dissolution in water of aluminum sulfate, aluminum chloride, aluminum bromide, ferric chloride, or potassium aluminum sulfate. Such solutions may, for example, be created by incorporating water and any one of the solutes listed above into separate compartments within a sealed packet, the compartments being separated via a frangible or otherwise releasable seal. Pressure upon the water compartment, for example, could break the frangible seal, allowing the water to mix with and dissolve the solute, creating an exothermic solution.

The thermally activated adhesives of the present invention may comprise a polymeric composition comprising a polymer which has a first-order melting transition between about 5 degrees C. and about 50 degrees C. Further, it is preferred that the transition occurs over a melting range of less than about 10 Celsius degrees, more preferably over a range of less than about 5 Celsius degrees. Such a range for the melting transition ensures that the transition from the tacky state to the substantially nontacky state (and/or vice versa) will be quite rapid. The melting transition preferably occurs in the range of about 20 deg. C. to about 40 deg. C., and most preferably in the range of about 25 deg. C. to about 37 deg. C. In alternative embodiments (e.g., thermally reversible adhesive embodiments), the polymeric composition has a freezing point lower than the deactivation temperature (e.g., skin temperature). The freezing temperature may be, for example, in the range of about 15 deg. C. to about 30 deg. C. In any case, the rate of freezing and the associated loss of adhesion, may be increased via the addition of seeding agents as known in the art.

The thermally activatable adhesive of the present invention may be a crystallizable polymer or a functional equivalent of a crystallizable polymer having a weight average molecular weight in the range of about 20,000 to 2,300,000 Daltons, typically 100,000 to 1,300,000 Daltons, and more typically 250,000 to 1,000,000 Daltons. Crystallizable polymers which may be used in the adhesive composition include both side-chain crystallizable and main-chain crystallizable polymers, the difference being that the former class of compounds contain crystallizable side-chain moieties and the latter class are rendered crystallizable by their backbone structure. Further, the polymer chains in the crystallizable polymer composition may optionally be crosslinked to provide greater physical stability of the adhesive. The adhesive composition may optionally include additives as known in the art, such as filers, tackifiers, antioxidants, and the like.

The adhesives of the present invention may be applied to or coated onto any substrate by any means known in the art. Suitable substrates are preferably breathable films as described herein for use as backsheets, polyolefinic films, nonwovens, highlofts, formed films, apertured films, and the like.

One exemplary thermally activatable adhesive is described as Example 1 in U.S. Pat. No. 5,387,450, which is incorporated by reference herein. The adhesive is prepared by combining 10 g of hexadecyl acrylate, 2 g of ethyl acrylate, 15 ml of deoxygenated toluene, and 0.06 g of AIBN as an initiator, and heating at 60 deg. C. under a nitrogen atmosphere for 12 hours. The resulting mass is extracted with ethanol and dried in vacuum to yield a rubbery mass. A sample of this material is heated to 70 deg. C. and pressed into a 0.001 inch-thick film. A sample of the film was placed onto the adhesive side of a standard pressure sensitive tape, and stored at 25 deg. C. The resulting tape is nontacky to the touch and exhibits no tack or adhesion to paper at room temperature. When the tape is placed on the wrist of a human subject, however, it becomes tacky almost instantly and exhibits good adhesion. When removed from the skin and kept at room temperature, the tape quickly loses its tack and adhesive properties. Other examples of thermally activated adhesives suitable for use in the claimed invention are described in more detail in U.S. Pat. Nos. 5,156,911 and 5,648,167; which are hereby incorporated by reference herein.

An exemplary thermally reversible adhesive is described as Example 2 in the above-referenced U.S. Pat. No. 5,387,450 and is prepared by mixing five percent w/w acrylic acid and 5% w/w ethylacrylatehexadecylacrylate copolymer (1 g) with 1 ml of toluene and 0.004 g XAMA 2 (Virginia Chemicals, Portsmouth, Va.) as a cross-linking agent. The material is allowed to stand two days at 80 deg. C. at which point it is more viscous. More toluene is added to make the solution spreadable. The mixture is then spread onto a microporous backsheet film, or other suitable substrate, dried at 80 degree C. for 1 hour, and allowed to cool. The film is easily removable from human skin by applying a cool, wet paper towel.

Figure 2:
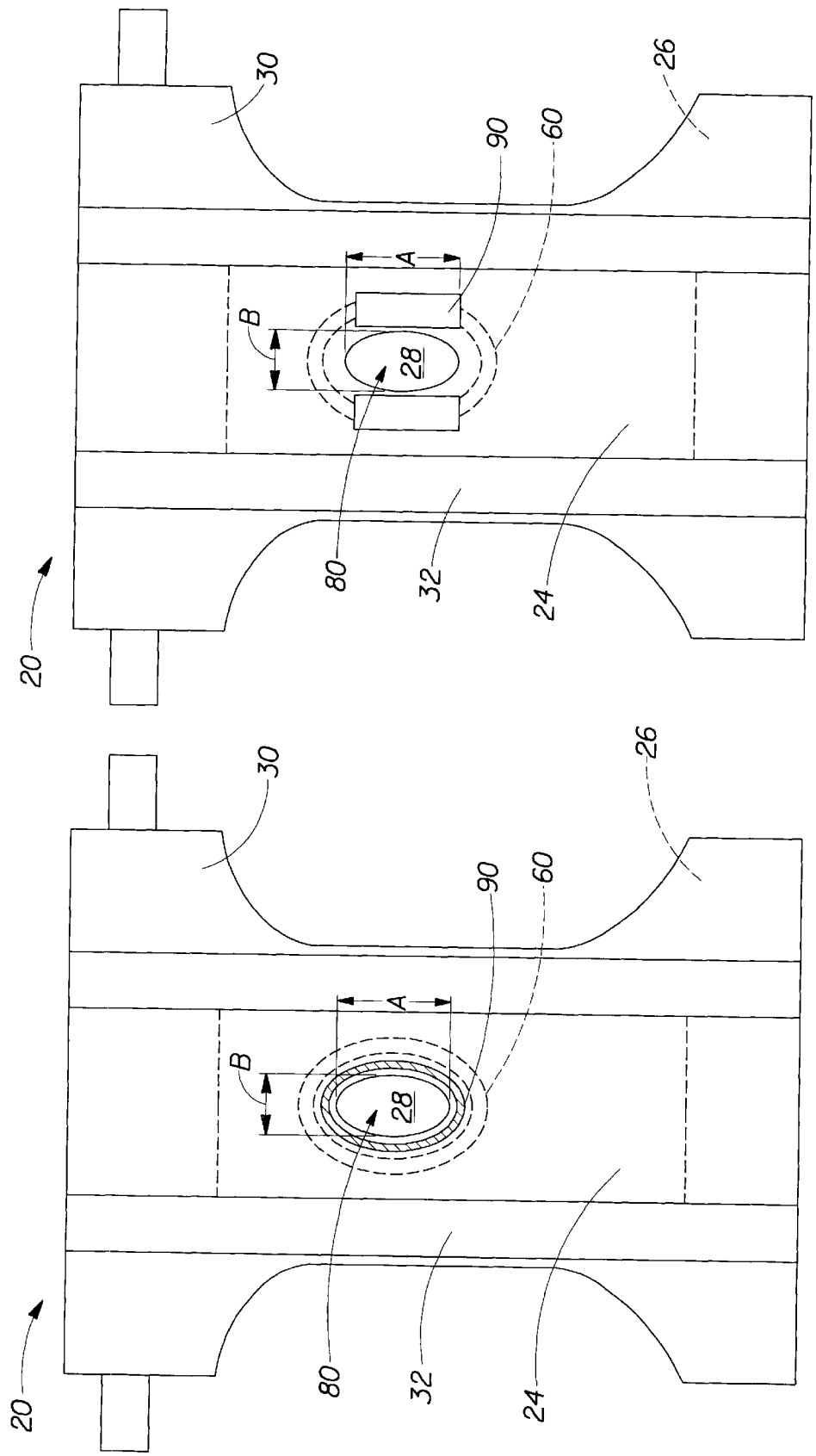
FIG. 2 is a plan view of a disposable diaper configuration of the present invention.

The thermally activatable adhesive 90 may be disposed on any portion of the article intended to be adhered to a wearer or another portion of the article or a different article. In one embodiment, as shown in FIG. 2, the thermally activatable adhesive 90 may be located on the topsheet 24 of the article 20. However, the thermally activatable adhesive 90 may also be integral with the material making up the topsheet 24 or other element of the absorbent article or may be a separate material disposed directly or indirectly on all or any portion of the absorbent article. Further, the thermally activatable topical adhesive 90 may be disposed on any portion of the absorbent article. For example, in FIG. 9, the thermally activatable adhesive 90 is shown in the waist and leg cuff regions of the article 20. The thermally activatable adhesive may be put on the article by any means and may be in any pattern or configuration including, but not limited to lines, stripes, dots, and the like.

Certain preferred embodiments of the present invention are particularly suited to the entrapment or encapsulation of bodily waste and thus reduce the amount and area of contamination of the wearer's skin by the waste. In order to achieve the desired level of performance, especially for viscous bodily waste such as feces, at least two functions should be performed. First, the diaper should have means of maintaining proximity of the accepting element of the diaper (e.g., an aperture in the topsheet) to the wearer's waste exit point (e.g., anus) of the wearer. By "aperture" it is meant any opening in the topsheet that may allow passage of waste from the wearer facing side to the garment facing side of the topsheet, including holes of any shape, slits and the like. The topsheet may also include elastic means suitable for foreshortening the topsheet in the longitudinal and/or other dimensions. Second, the diaper should provide a void space 70 for the waste even under applied pressures which are typical of those generated by a wearer on the crotch and buttocks regions of the article while the wearer is in a seated position. Both of these functions can be performed, for example, by a diaper as depicted in FIG. 2 which includes an apertured topsheet, spacing member and an adhesive to maintain the aperture in the region of the wearer's anus.

In order to provide a void space 70 which can be maintained under pressure, preferred embodiments of the present invention include one or more spacers or spacing members 60. The spacing member(s) 60 are intended to space the topsheet 24 or other covering layer away from the absorbent core 28 and/or other underlying layers such as sublayers, acquisition layers and the like. However, it is also contemplated that the spacing member 60 may space apart any other two elements of the diaper 20, including but not limited to the topsheet 24 and the backsheet 26, the acquisition layer and the core 28, the core 28 and the backsheet 26, etc. Nonlimiting, exemplary spacers 60 are disclosed in the patents incorporated by reference above.

The spacing member 60 may be of any suitable size and/or shape. In preferred embodiments, the spacing member 60 has a body facing side 62, a backsheet facing side 64 and a thickness T of between about 0.5 cm and about 3.0 cm in use. (As used herein, the thickness T of the spacer 60 is the distance between the body facing side 63 and the garment facing side 65 of the spacer 60.) Further, it is preferred that the spacer 60 create and maintain during use a void space 70 of between at least about 10 cubic cm and about 150 cubic cm, and preferably between about 25 cubic cm and about 75 cubic cm. It is also important that the lateral dimension X of the void space 70 be large enough to accommodate the feces, but narrow enough such that the spacing member 60 can support the ischia of the wearer. Preferably, the lateral dimension X of the void space 70, defined by the spacer 60 in the area corresponding to the anus of the wearer, is between about 1 cm and about 5 cm, and more preferably between about 1.5 cm and about 3.5 cm.

Although the shape of the spacer 60 is not critical, it has been found that elliptical and "keyhole" shaped spacers (e.g. the spacer shown if FIG. 4) perform particularly well. If such a spacer 60 is implemented, it is preferred that the spacer 60 be disposed generally in the crotch region 37 of the diaper 20 and oriented such that the first region 120 of the spacer 60 is located toward the front waist of the diaper 20 when worn and the second region 125 of the spacer 60 is located toward the rear waist of the diaper 20 when worn. Alternatively, U-shaped spacers may be suitable for use in certain embodiments (preferably with the open end of the U-shape oriented toward the rear waist region of the diaper 20 when worn). In any case, the spacer 60 may be unitary or may comprise a multiplicity of separate or operatively associated parts. Further, the spacer 60 may have a closed perimeter 65 or may comprise openings, holes, or channels extending from the fecal void space 70 through the spacer wall 62 to the perimeter 65 of the spacer 60. Such embodiments may be useful to allow distribution of feces from the void space 70 to other parts of the diaper 20.

The spacing member 60 may comprise any material or combination of materials which are suitable for use in an absorbent article to be worn by a human wearer. For example, the spacing member 60 may include foams, woven or nonwoven webs, thermoplastic materials, organic materials, fibers, gels, rubber or synthetic rubber, etc. In one preferred embodiment, the spacing member 60 comprises an absorbent foam made from a 16:1 water/oil emulsion, having a glass transition temperature of about 10° C., and having a compression of about 40% in a dry state and about 30% in a wet state (i.e., when saturated with water) under about 1.0 psi applied pressure. Thus, in certain embodiments, the compression under about 1.0 psi in the wet state may be less than the compression under about 1 psi in the dry state.

In a preferred embodiment, the spacing member 60 is relatively soft, but resilient and capable of withstanding the forces typical of a baby's movements and/or the weight of a baby sitting or lying on the spacing member 60. Thus, the spacing member 60 should be capable of withstanding at least 0.5 psi and preferably at least about 1.0 psi while compressing no more than about 60%, and preferably no more than about 30% in both wet and dry conditions.

In yet another embodiment, the spacing member 60 may be triggered during use. That is, the spacing member 60 may be stored in the diaper 20 in one configuration and may be triggered by some event or material which changes the configuration of the spacing member 60 or the surrounding structure so as to provide the diaper 20 with a desired configuration for receiving and/or storing bodily exudates.

For example, the spacing member 60 may include a material which expands when contracted by water, urine, feces, enzymes or other means associated with the wearer's body or bodily exudates. Changes in temperature, pH and saline concentration are also "triggers" which can change the spacing member 60. Thus, when the wearer urinates, the spacing member 60 may increase in thickness, change shape or otherwise orient itself in the diaper 20 to provide a void space 70 into which urine and/or feces can flow.

In preferred embodiments, at least a portion of the spacing member 60 is joined to the topsheet 24. This helps keep the primary aperture 80 aligned with the void space 70 of the spacer 60 during use. It is also preferred that at least a portion of the spacer 60 be joined with at least a portion of the structure which underlies the spacer 60, such as the core 28, a sublayer or the backsheet 28. In any case, the spacer 60 may be joined directly or indirectly by any means known in the art. Typical joining means include adhesives, heat, pressure, static, magnetism, snaps, hook and loop fasteners and the like.

The advantages of a diaper including an apertured topsheet and a spacing member 60 are significantly reduced if the aperture 80 does not stay aligned with the wearer's anus and the void space 70 provided by the spacer 60 throughout the time of use (or at least until the wearer has a bowel movement). Accordingly, the diaper 20 of the present invention is preferably provided with a means for maintaining the aperture 80 in alignment with the wearer's anus. In certain preferred embodiments, the diaper 20 includes a thermally activatable adhesive 90, as described above, which acts to hold the aperture 80 in place during use. As shown in FIG. 2, the thermally activatable adhesive 90 may be located on the topsheet 24. However, the thermally activatable adhesive 90 may also be integral with the material making up the topsheet 24 or other element of the absorbent article or may be a separate material disposed directly or indirectly on all or any portion of the absorbent article. Further, the thermally activatable adhesive 90 may be disposed on any portion of the absorbent article in any pattern or configuration including, but not limited to lines, stripes, dots, and the like.

Figure 3:
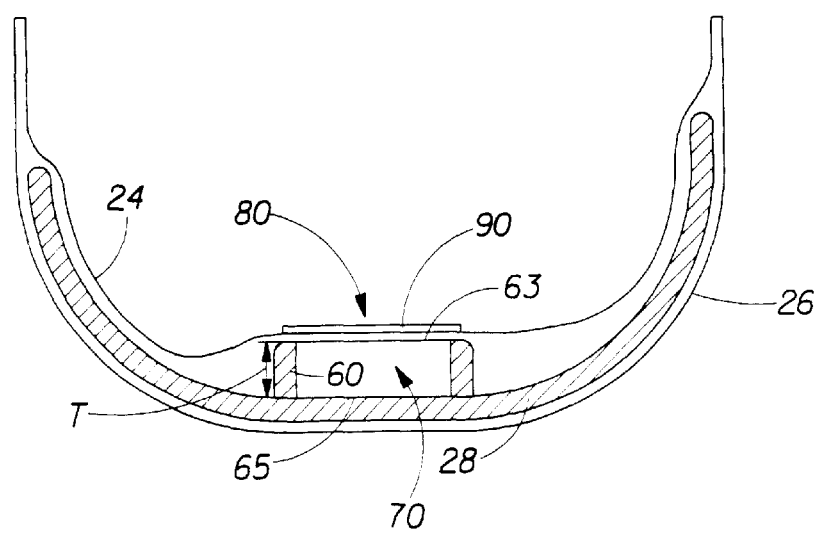
FIG. 3 is a cross-sectional view of one embodiment of the present invention shown as it may appear when worn.

In one preferred embodiment, shown in FIGS. 2 and 3, the thermally activatable adhesive 90 is disposed on the topsheet 24 around the entire perimeter of the aperture 80. However, embodiments are contemplated wherein the adhesive 90 surrounds only a portion of the aperture 80 and/or is disposed in locations not directly adjacent the aperture 80, such as around the edge of the topsheet 24, on the leg cuffs 32 or in one or both of the waist regions. Alternatively, adhesive 90 may be disposed on the spacer 60 itself. If this is done, the adhesive 90 may be on an exposed surface of the spacer 60 or may be located beneath an apertured, slit or otherwise reticulated layer such that the adhesive 90 can contact the wearer in use.

One alternative embodiment of the present invention is an absorbent article as is generally shown in FIG. 2A. The absorbent article 20 is provided with a nonwoven topsheet 24 (e.g., P-8 available from Veratec, Inc.) including an elliptical aperture 80 having an open area of about 17 cm². (As used herein the term "open area" refers to the plan view area of the aperture.) In a preferred embodiment, the aperture 80 has a longitudinal dimension A of about 6 cm and a lateral dimension B of about 3.5 cm. The aperture 80 is preferably located in approximately the area of the diaper 20 associated with the wearer's anus. A thermally activatable adhesive 90 is applied to the topsheet 24 about at least a portion of the aperture 80 in about a 1.5 cm wide band. The adhesive 90 comprises a thermally activated adhesive disposed on a vapor-permeable film carrier cut in the shape of the aperture from a sample PRE-PO Incise Drape available from Landec Labs, Inc. of Menlo Park, Calif. The film layer side of the sample is affixed to the perimeter of the aperture on the wearer-facing side of the topsheet with double-sided tape, exposing the thermally activated adhesive to the wearer's skin during use.

Figure 4:
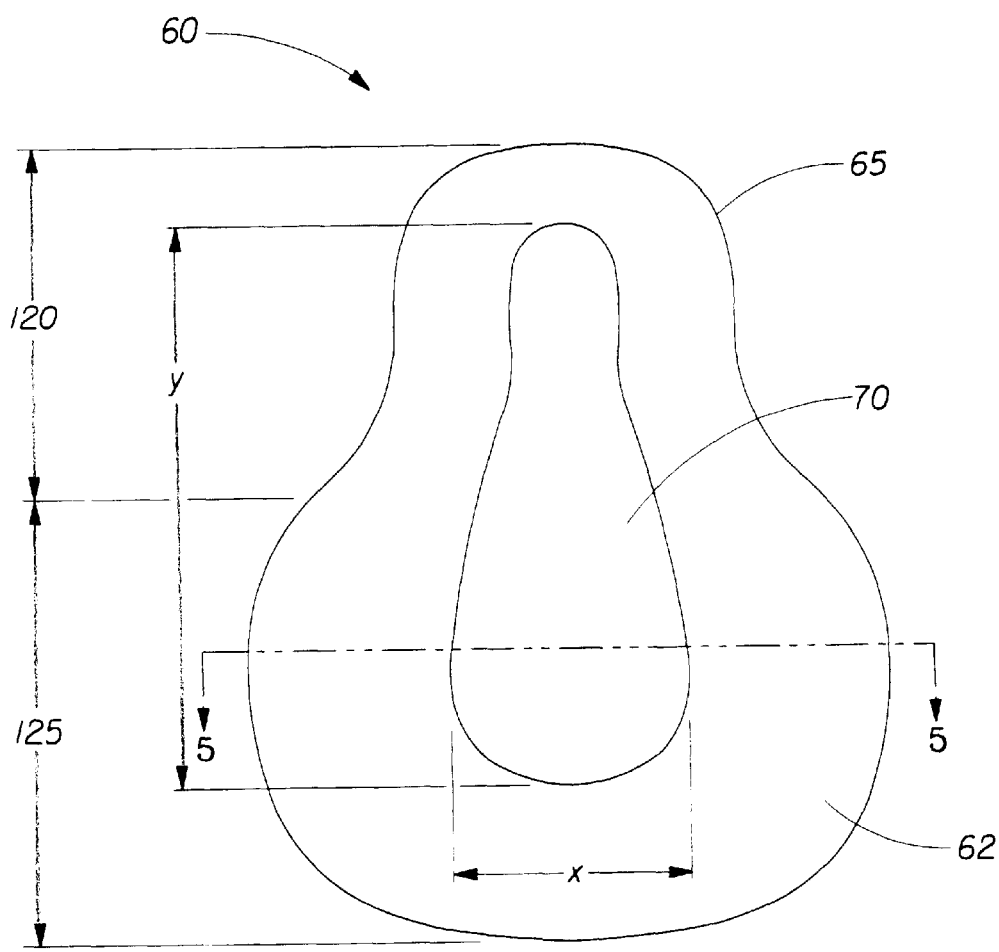
FIG. 4 is a plan view of a spacing member suitable for use with the present invention.
Figure 5:
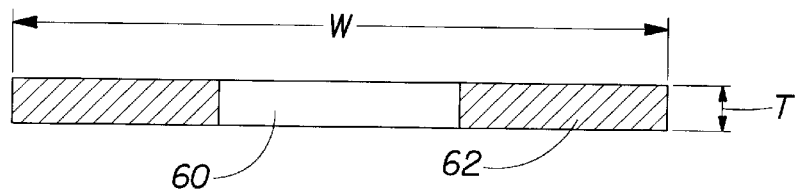
FIG. 5 is a cross-sectional view of the spacing member shown in FIG. 4 taken through section line 5—5.

An absorbent foam spacer 60 is disposed between the topsheet 24 and the backsheet 26 and is affixed to the underlying structure (e.g. core 28) of the diaper 20 such that the void space 70 created by the spacer 60 is aligned with the aperture 80 in the topsheet 24. The spacer 60 has a "keyhole" geometry, as shown in FIG. 4. Further, the spacer 60 has a thickness T of about 1.25 cm, a void space area of about 24 $cm^2$, a width W of about 3.5 cm in the region corresponding approximately to the anus, and a void space volume of about 33 $cm^3$. (As used herein the term "void space area" means the plan view area of the void space 70. Void space volume as used herein is the volume of the void space created by the spacer 60.) The void space 70 preferably has a length Y of about 8.4 cm and a width X of about 3.9 cm. The spacer 60 preferably compresses no more than about 60%, more preferably 30% under a 1.0 psi load when the spacer 60 is in a dry state, and no more than about 60%, more preferably 30% under a 1.0 psi load when wet or saturated (e.g., with water).

The spacer 60 preferably includes an absorbent foam made from a 16:1 water/oil emulsion, having a glass transition temperature of about 10° C., and having a compression of about 43% dry and about 32% wet under about 1.0 psi applied pressure. The absorbent foam is die cut into two 0.625 cm thick layers having the "keyhole" shape shown in FIG. 4. The two layers are then stacked on top of each other such that the void space 70 of each layer is aligned. The walls 62 of the dual layer foam spacer 60 are preferably wrapped in strips of a nonwoven (e.g. P-8). At least a portion of the spacer 60 is attached to the absorbent core 28. (The spacer 60 may be also or alternatively joined with another underlying element such as a sublayer, a secondary topsheet or the backsheet). It is also preferred that the spacer 60 be joined to the topsheet 24 along some or all of the spacer's perimeter 65. This helps keep the aperture 80 in the topsheet 24 aligned with the void space 70 of the spacer 60 during use.

Figure 6:
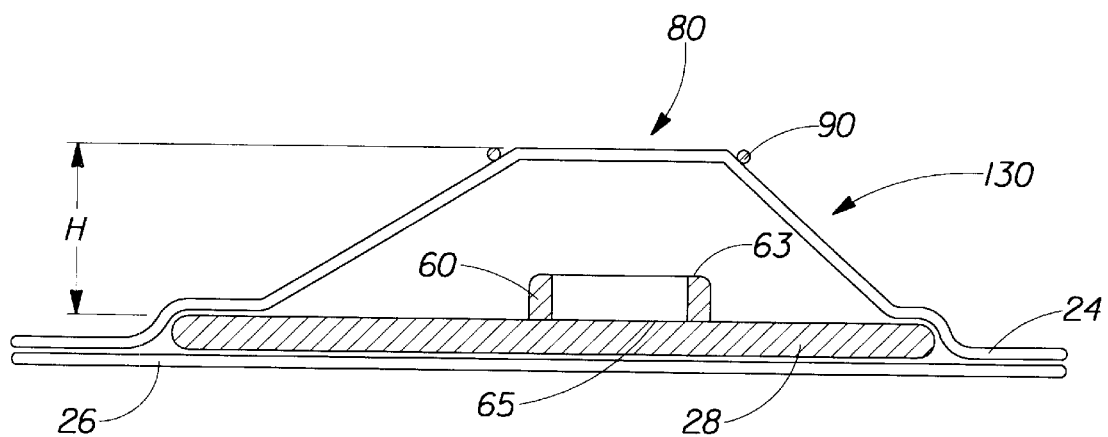
FIG. 6 is a cross-sectional view of one embodiment of the present invention.

In an alternate embodiment, as shown in FIG. 6, the topsheet 24 may be configured so at to provide a cone 130 structure when worn. As shown in FIG. 6, the cone structure is formed when the topsheet is pulled away from the core until it is restrained by an attachment to an underlying layer, such as a secondary topsheet, spacer, core, or backsheet. The cone structure 130 preferably has a height H (the height is defined as the distance above the backsheet facing side of the spacer the to which the aperture 80 of the topsheet 24 may be raised under a force of less than 100 grams when the diaper 20 is in a flat configuration). The height H should not be too great or application may become difficult (i.e., the caretaker may have to take extra care or time to align the top of the cone 130 to the wearer's waste source region) or so that the cone 130 can fold over on itself during wearing and block the aperture 80. Conversely, the height H should not be too small or there may not be enough volume in the cone 130 to handle any overflow from the spacer's void space 70. A height H of between about 1.0 cm and about 10 cm is generally suitable. Preferably the height H is between about 2 cm and about 7 cm.

In alternative embodiments, for example those which do not include a spacer or aperture, the thermally activatable adhesive 90 may be a topical adhesive providing at least temporary attachment of the article, or a portion thereof, to the wearer's skin. In these embodiments, the thermally activatable adhesive 90 may be located on any body-contacting surface of the product. In certain preferred embodiments, the thermally activatable adhesive is located in proximity to the perimeter of the article, such as the side margins, leg cuffs, or waist region, especially in the laterally outboard portions of the waist regions, and most preferably in the laterally outboard portions of the rear waist region. The thermally activatable adhesive 90 may be applied in a solid film coating or in any pattern, including stripes, circles, squares, polygons, series of dots or other regular shapes, or irregular swirls or stripes such as random or irregular patterns of adhesive including but not limited to spirals or random line/fiber patterns.

Figure 10:
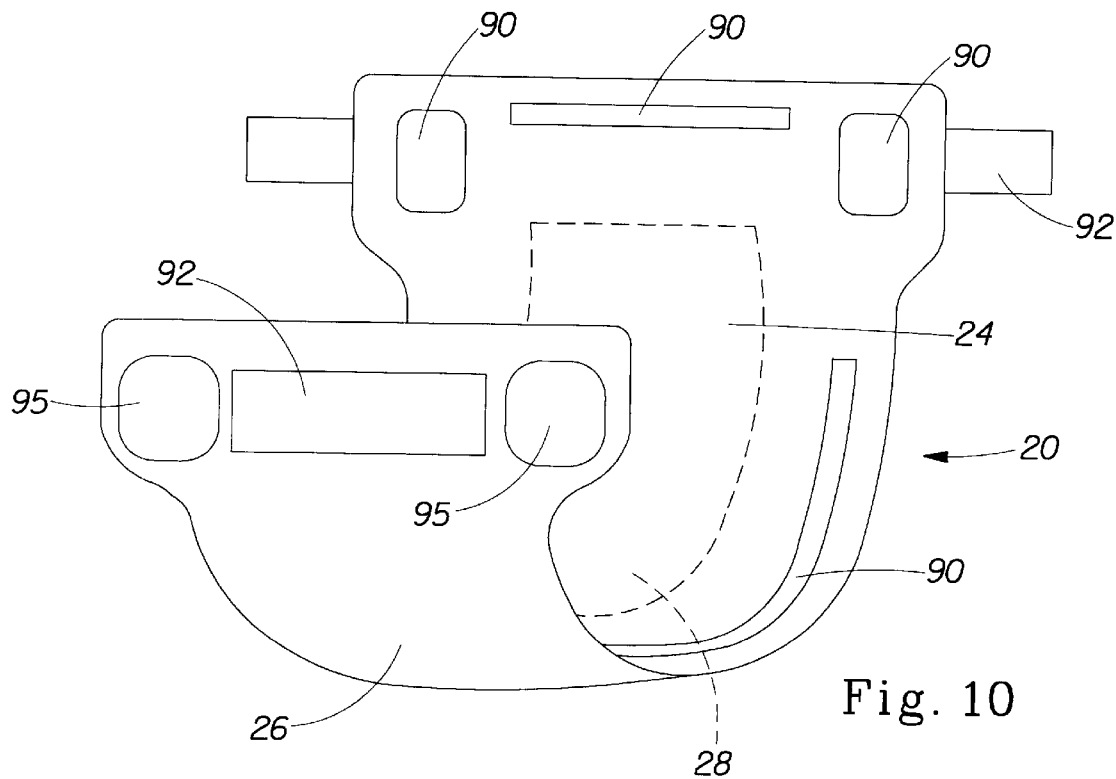
FIG. 10 is a schematic view of one embodiment of the present invention in the form of an absorbent article.

In some embodiments, the activatable adhesive may be used to provide a temporary attachment between the article and the wearer, or between different parts of the article or between two or more different articles. Such a temporary attachment may be useful, for example, in articles designed with the option of being applied to the wearer with the wearer in a standing position. In such embodiments, the activatable adhesive 90 is preferably positioned on a wearer-contacting surface of the article such that it can at least temporarily hold the article in place against the wearer's skin while the caregiver or wearer completes configuring the article to its intended construction or configuration for wearing. One embodiment of the present invention suitable for such use is shown in FIG. 10. The temporary attachment can also provide time for the wearer or caregiver to fasten the article about the wearer or the another article by means of the primary fastening system to be used throughout the wearing cycle of the article (e.g. tape or hook and loop fasteners). Generally, once the fastening system is fastened, the activatable adhesive 90 may be deactivated.

In one embodiment, a thermally activatable adhesive 90 is disposed near the laterally outboard portion of the back waist region of a diaper. (Preferably, the activatable adhesive 90 is thermally reversible, as described above). The activation temperature is preferably above the wearer's skin temperature. To apply the article, the caregiver may activate the adhesive and place the portion of article including the activatable adhesive against a predetermined portion of the wearer's skin. (For example, the adhesive may be applied adjacent the wearer's back waist region, the wearer's hips, and/or the wearer's buttocks.) The caregiver then configures the remainder of the article about the wearer and fastens the primary fastening system of the article. The thermally reversible adhesive is then cooled and deactivates. As noted above, suitable activation temperatures for such temporary attachment users are generally between about 33° C. and 60° C., preferably between about 37° C. and 49° and more preferably between about 39° C. and 45° C.

In further alternative embodiments, the thermally activatable adhesive 90 may be a topical adhesive providing improvements to the fit of the product during wearing by providing at least some additional resistance to the diaper slipping downward or moving in other undesirable ways in use (i.e., providing a higher effective coefficient of friction between the product (i.e., adhesive) and the wearer's skin). In these embodiments, the thermally activatable adhesive 90 may be located on any body-contacting surface of the product. Preferred locations for the thermally activated adhesives are disclosed in co-pending U.S. patent application Ser. No. 09/312,997 entitled "Disposable Absorbent Article Having Article Retention Zones" filed May 17, 1999 in the names of Gregory Ashton et. al. as the locations for the garment retention zones. The above identified patent application is hereby incorporated by reference herein.

Figure 7:
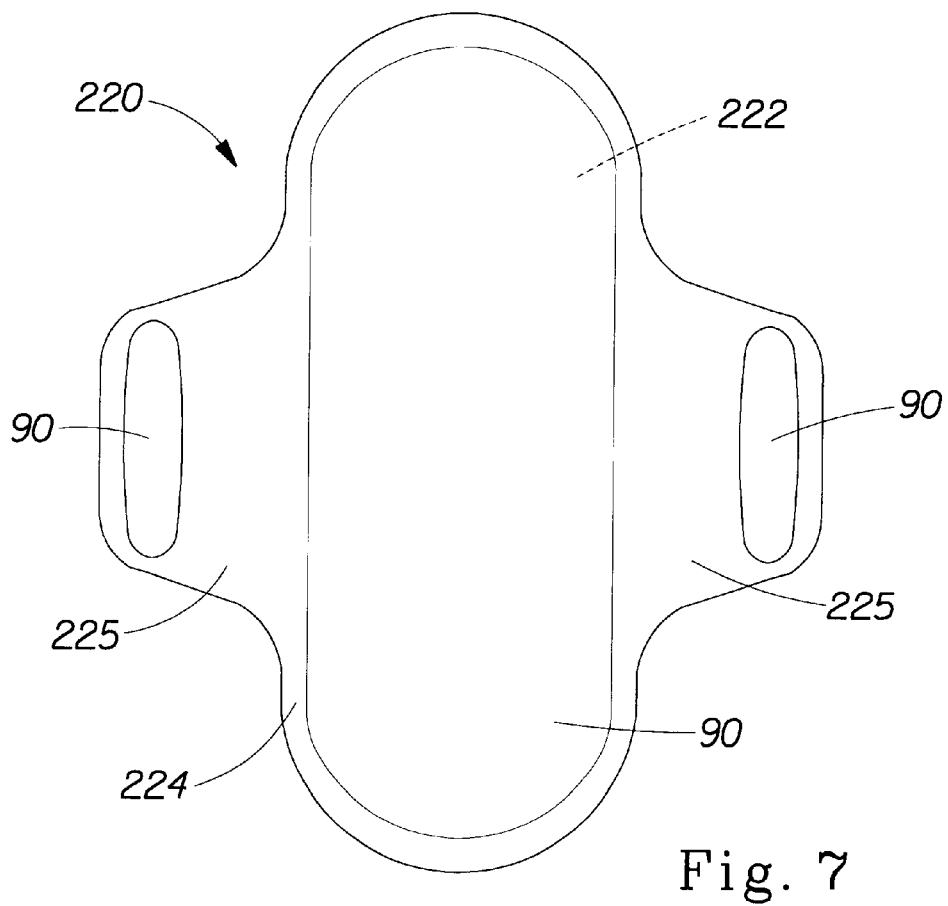
FIG. 7 is a plan view of an alternative embodiment of an absorbent article of the present invention.
Figure 8:
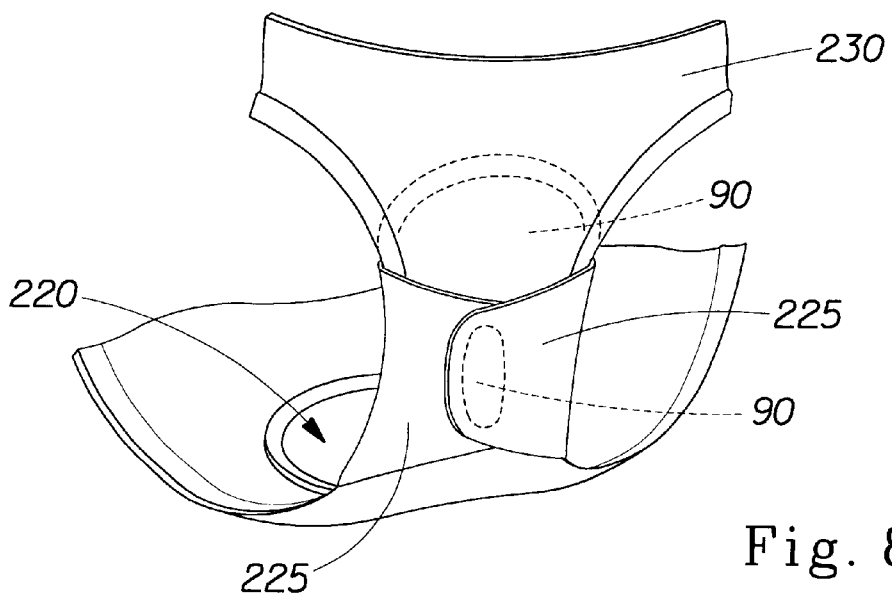
FIG. 8 is a perspective view of the article of FIG. 7 shown as it would be worn by a wearer.
Figure 9A:
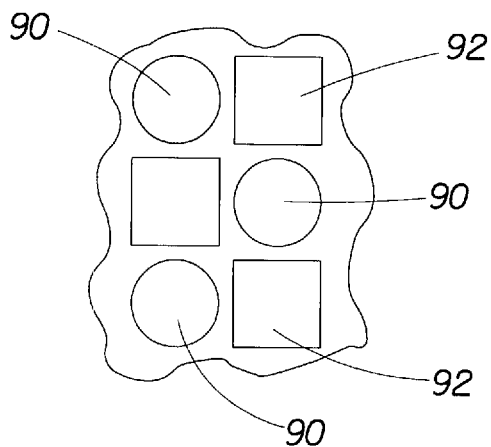
FIGS. 9A–9E are plan views of alternative embodiments of fastening systems suitable for use with the present invention.
Figure 9B:
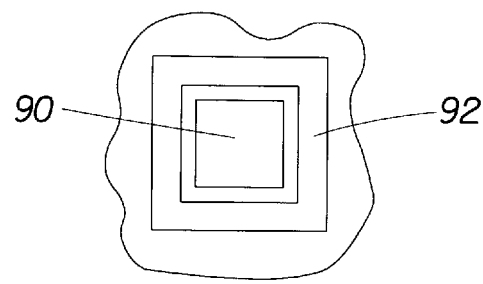
Figure 9C:
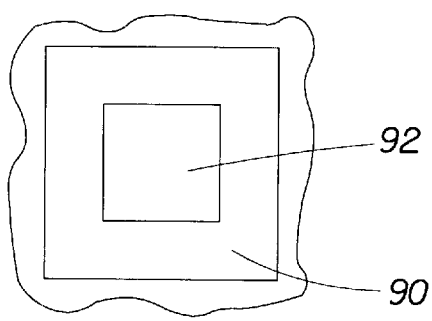
Figure 9D:
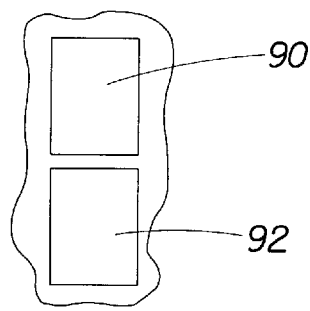
Figure 9E:
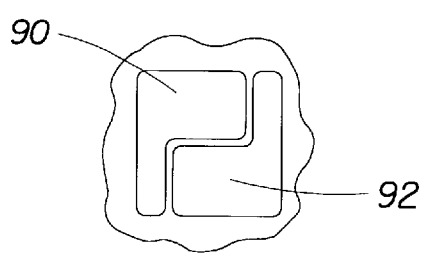

In further alternative embodiments, the thermally activatable adhesive 90 may serve as the primary or secondary fastening system or a component thereof (see, for example, FIG. 10). For example, the thermally activatable adhesive 90 may function as an adhesive tape tab fastener for a diaper. Further, the thermally activatable adhesive 90 may be used in conjunction with a sanitary napkin or other feminine protective device. One such device is shown in FIGS. 7 and 8. The sanitary napkin 220 has a topsheet 222, a backsheet 224 and wings 225. (It should be noted that the sanitary napkin need not have wings to function in accordance with the present invention.) As shown, the thermally activatable adhesive 90 may be disposed in the backsheet 224, the wings 225, or both. The adhesive 90 can act to connect the wings 225 or flaps of the sanitary napkin 220 to each other around the wearer's underwear 230, may alternatively connect the wings 225 is or flaps directly to the wearer's underwear 230, may attach the main body of the sanitary napkin to the wearer's underwear 230, or may be used as an adhesive for disposal of the article. In yet other embodiments the adhesive 90 may be disposed on the topsheet 222 or other body-facing surface so as to adhere the article directly to the wearer's skin or to another article or device. Typical sanitary napkins are described in U.S. Pat. No. 4,589,876 issued to Van Tilburg, May 1986; 4,687,478 issued to Van Tilburg Aug. 18, 1987; and 5,009,653 issued to Osborn on Apr. 15, 1991. Example of interlabial feminine protection devices are disclosed in U.S. Pat. No. 5,762,644 issued to Osborn et. al. on Jun. 9, 1998. Each of these patents is incorporated herein by reference.

Alternatively, the thermally activatable adhesive may be used in conjunction with any type of primary fastening system 92 as described herein to supplement its fastening strength, thereby increasing the resistance to removal versus the use of the primary fastener alone. Preferably, in these embodiments, the thermally activatable adhesive 90 increases the peel and/or shear strength of the fastener by at least about 10%, more preferably by at least about 25%, even more preferably by at least about 50%, and most preferably by at least about 100%. The activatable adhesive in such embodiments may be part of or separate from the primary system. The thermally activated adhesive 90 may be placed laterally inward or laterally outboard of the primary system, longitudinally above or below the primary system 92, or even be coincident or interleaved with the primary system. One exemplary approach to placing the thermally activated adhesive 90 coincident with the primary system 92 is disclosed in publications WO 95/25905 and WO 98/10728, each of which is incorporated herein by reference. The thermally activated adhesive 90 can replace the cohesive portion of the 2-mechanism mechanical-cohesive system described in WO 95/25905 on either the hook portion, the loop portion, or both portions of the 2-mechanism system. Alternatively, the thermally activated adhesive 90 may replace the bonding element at the base of the loops described in WO 98/10728, which is incorporated by reference herein. Yet another embodiment of coincident systems places one or more regions of temperature activated adhesive 90 among one or more other fasteners, examples of which are shown in FIGS. 9A–9E.

In alternative embodiments, the thermally activatable adhesive 90 may be used in conjunction with any type of primary fastening system to control the relative position of is parts of the article not directly controlled by the primary fastening system. In such fastening systems on a diaper, the temperature activated adhesive 90 may reduce shifting of any overlapping portions or components of the diaper or to improve fit. In such embodiments, the temperature activated adhesive 90 may be used as the primary fastening system, the secondary fastening system, or for both fastening systems. Likewise, a sanitary napkin may comprise a standard pressure sensitive adhesive for attachment of the pad to the wearer's underwear, and a thermally activatable adhesive 90 for attachment of the protective wings to the underwear or a thermally activatable adhesive 90 for attachment to the wearer's underwear and a standard pressure sensitive adhesive for attachment of the protective wings to the underwear or each other. Embodiments are also contemplated wherein the thermally activatable adhesive 90 functions as the primary fastener, and other fasteners (e.g., pressure sensitive adhesives, mechanical fasteners, etc.) function as a secondary fastener.

In certain embodiments, the thermally activatable adhesive 90 may be disposed on the article to adhere a portion of the product to itself. In such cases, the article may include at least one adhesive receiving zone 95, one example of which is shown in FIG. 10. The thermally activatable adhesive receiving zone 95 is the location at which the thermally activatable adhesive 90 adheres one portion of the article to another portion of the article. The relative positions of the thermally activatable adhesive 90 and the adhesive receiving zone 95 can vary. For example, the thermally activatable adhesive 90 may be disposed on the body facing surface of the product and the adhesive receiving zone 95 may be disposed on the outer surface of the product. Alternatively the adhesive receiving zone 95 may be disposed on the body facing surface of the product and the thermally activatable adhesive 90 may be disposed on the outer surface of the product. Further, the adhesive receiving zone 95 and the thermally activatable adhesive 90 may both be disposed on the body facing surface of the product or both be disposed on the outer surface of the product. In any case, the adhesive receiving zone 95 may be a separate piece or material added to the diaper or may be integral to a part of the diaper, including but not limited to the topsheet, the backsheet, the leg cuff, or the waistband.

In embodiments in which it is desirable for the activatable adhesive 90 to be active during the wearing period and in which the activatable adhesive 90 is thermally activatable and deactivatable, it is preferred to have the activation and deactivation temperature at or slightly below body temperature such that the heat of the wearer's body alone can maintain the adhesive in its active state during the wearing period. If the activation or deactivation temperature is above body temperature, it may be necessary to supply additional heat to the adhesive during the wearing period to maintain sufficient adhesive strength during the wearing period. Thus, activation and deactivation temperatures for thermally reversible adhesives intended to remain active in use are generally between about 25° C. and 38° C., preferably between about 28° C. and 38° C., and even more preferably between about 30° C. and 37° C.

In further alternative embodiments, the thermally activatable adhesive 90 may be positioned to help maintain the product in a closed, wrapped configuration for disposal. Embodiments previously disclosed herein in which the temperature activatable adhesive 90 is disposed on the body facing surface of the product can readily utilize the temperature activatable adhesive 90 for disposal (e.g., the diaper shown in FIG. 10). However, the activatable adhesive may also or alternatively be disposed on the outer surface of the article in a position to maintain the product in a disposal configuration. Further, when the thermally activatable adhesive 90 is positioned on the-product as in U.S. Pat. No. 5,019,065 (in place of the standard adhesive portion), the thermally activatable adhesive 90 can be used to secure the product for disposal. The thermally activatable adhesive 90 may be used with many tape designs to secure the product for disposal, including disposal tape systems disclosed in U.S. Pat. Nos. 5,108,384; 4,869,724; 5,575,784; 5,626,573; and 5,279,604 and publications WO 98/53780 and WO 99/17693. Each of these patents is incorporated by reference herein.

In additional alternate embodiments, the article may comprise the heat source for the activation of the adhesive (i.e., the article may contain its own heat source and not be reliant on body-temperature activation). In these embodiments, the heat source may comprise any device or material which generates a heating effect. For example, the heat source may generate a temperature change via any internal power source, such as battery or solar powered heaters, an exothermic chemical reaction, latent heat from phase changes, or a separable, potentially re-usable, heat pack. Further, the heat source may generate a temperature change using a thermoelectric effect such as the Peltier Effect or via resistive heating. Alternatively, the heat source may include a heat storage device which is heated to a high temperature by some external device and can maintain a relatively high temperature for a period of time.

In embodiments employing latent heat from phase changes to activate the thermally activatable adhesive, heat may be released during solidification of, for example, a super-cooled or super-saturated fluid solution. Since phase changes are reversible, this type of heat source may be re-usable (i.e., the heat source may be re-used on other absorbent articles). Additionally, it may be desirable to remove the heat from the article after activation of the adhesive to limit contact of the heated item with the skin in the region of the article containing the activatable adhesive. Also, it may be desirable to have the heat pack reusable for cost or other reasons. A suitable heat source utilizing the latent heat from a phase change is available as the Re-Heater Heat Pack marketed by Source Marketing International, INC. of Dallas, Tex. Additional suitable heat sources based on latent heat release during phase changes are described in and U.S. Pat. Nos. 5,805,766; 5,476,490; 5,662,096; 4,077, 390; 5,897,580; 5,736,110; 5,275,156; 4,460,546; 4,899, 772; 4,580,547; 5,056,589; 5,143,048; 708,549; 3,643,665; 3,951,127; and 4,451,383, all of which are incorporated herein by reference. Other systems which create exothermic effects are described in more detail in U.S. Pat. Nos. 4,462,224; 5,792,213; 5,545,197; 5,423,996; 5,552,075; and 5,650,090, all of which are incorporated herein by reference.

In embodiments wherein the heat source is a heat storage device, any suitable materials may be included in the heat storage device, but solid and liquid forms are preferred over gaseous forms as solids and liquids best maintain the desired low temperature when separated from the external heating system. Further, if solid materials are used, relatively small particles are preferable to allow the packet to be flexible to conform to the surface of the article and provide greatest contact with the activatable adhesive 90. Preferably, the particles are less than about 10 mm in their largest dimension, more preferably less than about 5 mm, and most preferably less than about 1 mm. The heat storage device may contain typical absorbent materials (including wood pulp fibers, cellulose fibers, superabsorbent polymers, sponges, foams, etc.) containing at least a low level of water (e.g., preferably less than about 5 to about 10% by weight), or may contain small particles of other suitable materials including but not limited to polypropylene, polyethylene, nylon, steel, polystyrene, rubber, and the like. Alternatively, the heat storage device may contain a gel or a liquid such as water, ethylene glycol, or any other liquid or gel. Exemplary heat storage devices are described in U.S. Pat. Nos. 4,920, 964; 4,891,501; and 5,417,276; All of which are incorporated herein by reference. Other suitable heat storage products are available under the names "Hot n' Cold Pack" from Sunbeam-Oster Household Products of Schaumburg, Ill.

U.S. Pat. Nos. 4,741,338; 4,860,748; 5,197,294; 4,483, 021; 4,470,263; and 5,800,490 describe thermoelectric heating devices which utilize the Peltier Effect and are suitable for activating a thermally activatable adhesive. All of these patents are incorporated herein by reference. The power source for the Peltier heating device may be any suitable power source including household AC power, a battery, or solar power. The Peltier heating device may be separable from the article, durably attached to the article, or merely a separate device that is held up to a portion of the article or near the wearer's skin as needed and does not in any way attach to the article or the wearer's skin.

In yet other heat source embodiments, other electric power may be used to create a heating effect by mechanisms other than the Peltier effect, such as, but not limited to resistive heating. U.S. Pat. Nos. 5,486,680; 4,665,308; 5,772,185; 4,705,935; and 5,230,333 describe electric powered heating devices which are also suitable for activating a thermally activatable adhesive. All of these patents are incorporated herein by reference The power source for the heat source may be household AC power, a battery, or solar. The heat source may be separable from the article, durably attached to the article, or merely a separate device that is held up to a portion of the article or near the wearer's skin as needed and does not in any way attach to the article or the wearer's skin. Further, the heat source may include a combination of heat generating mechanisms, such as both chemically based (chemical reaction or phase change based) and electrically powered heat generation. A suitable combination heat source system is disclosed in U.S. Pat. No. 5,805,776 which is incorporated herein by reference.

As described above, the heat source may comprise an exothermic chemical reaction. The exothermic chemical reaction may be an oxidation reaction driven by exposure of a suitable chemical system to air or other activating ingredient or ingredients. Suitable oxidative exothermic heat source are described in U.S. Pat. Nos. 5,741,318, 5,918,590, and pending U.S. application Ser. No. 08/623,752 filed Mar. 3, 1996 which discloses addition of water to the heat cell to activate the exothermic chemical reaction. The exposure of the oxidative chemical system to its activating ingredient(s), typically air or water, may be accomplished by any known means including removal of an impermeable seal or cover or by physically breaking a seal or portion of the cell. The mechanism of exposing the oxidative chemical system to its activating ingredient(s) may also involve an additional step for the user (e.g., removal of a seal), or be a result of normal handling of the product during the process of applying it to a wearer.

The heating device or any portion thereof may be disposable or reusable. For example, in some embodiments the heating device may be reused repeatedly utilizing the same mechanism for creating a heating effect in each re-use. In other embodiments the heating device may include one mechanism to generate a heating effect on one use and another mechanism on subsequent uses. For example, the heating device may utilize an exothermic reaction to generate a heating effect on one use and then may be reused as a heat storage device.

In any case, the heating device may be permanently joined to the article or removable therefrom. A removable heating device may be constructed either by including frangible bonds to facilitate heating device removal from the article or by attaching the heating device to the article with separable fasteners, including pressure sensitive adhesive fasteners, mechanical fasteners, hook and loop fasteners, interlocking fasteners, or any other suitable fasteners. Alternatively, the article may include a pocket or other structure into which the cooling device may be placed. Further, however, the heating device need not actually be connected to the product at all, but merely be held in place by the caregiver or wearer when needed to activate the thermally activatable adhesive. Removable heating devices, may be constructed in various forms, including small packets which the user fills a bladder or packet with hot water or other fluid, solid or gel materials and attaches it to the article in the region containing the thermally activatable adhesive, or may utilize any of the reusable heating device embodiments previously discussed. Further, the heating device may be applied to or held near the portion of the article including the thermally activatable adhesive after the article is in position on the wearer's body or at any time during application of the article to the wearer or during the wearing period.

Adhesion Method

Figure 11:
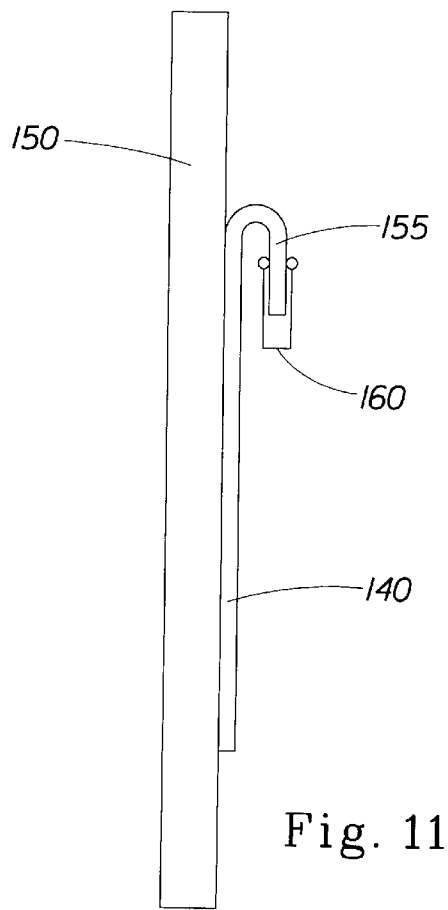
FIG. 11 is a schematic view of a portion of the apparatus used to measure adhesion.

A one-inch wide by 3¼ inch long sample 140 of the adhesive is applied to a smooth stainless steel plate 150 along 3 inches of its length, leaving a ¼ inch "lip" 155 free to pull in the adhesion test. A pressure of 3.3 psi is applied to the adhesive in the 3 inch long region in which it is adhered to the stainless steel plate (i.e., not in the "lip" region) for a duration of one minute. The stainless steel plate 150 should be held at the temperature at which the measurement for adhesion is being sought. (e.g. if one is trying to determine the adhesision value of a particular adhesive at 23 degrees Celcius, the plate should be held at a temperature of 23 degrees Celcius.). The "lip" is grasped in a clamp 160 attached to a Stevens-Farnell QTS-25 Texture Analyzer, model 7113-5 kg (available from Leonard Farnell Co. of Hatfield, England). The sample 140 is pulled by the Texture Analyzer at a 180° angle (as shown in FIG. 11) at a constant rate of 10 inches per minute. The adhesion value for the sample is the average resistance to the peel motion recorded by the Texture Analyzer over the length of the sample.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An absorbent article having a first waist region, a second waist region and a crotch region located between the first waist region and the second waist region, the absorbent article comprising:
    a topsheet,
    a backsheet joined with at least a portion of the topsheet,
    an absorbent core disposed between at least a portion of the topsheet and the backsheet,
    a thermally activatable adhesive disposed on at least a portion of the article, and
    a heat source to activate the adhesive.

2. The absorbent article of claim 1 wherein the thermally activatable adhesive is disposed in the first waist region of the article.

3. The absorbent article of claim 1 wherein the thermally activatable adhesive is disposed in the second waist region of the article.

4. The absorbent article of claim 1 wherein the thermally activatable adhesive is disposed in the crotch region of the article.

5. The absorbent article of claim 1 further comprising at least one leg cuff extending through at least a portion of the crotch region, wherein the thermally activatable adhesive is disposed on the leg cuff.

6. The absorbent article of claim 1 further having a body facing surface upon which the thermally activatable adhesive is disposed.

7. The absorbent article of claim 1 further having an outer surface upon which the thermally activatable adhesive is disposed.

8. The absorbent article of claim 1 wherein the thermally activatable adhesive provides a means to hold the article in a configuration for disposal.

9. The absorbent article of claim 1 wherein the thermally activatable adhesive disposed on the article is capable of being in contact with the skin of a wearer during at least some period of time during the article's use.

10. The absorbent article of claim 1 further including an adhesive receiving zone positioned to engage the thermally activatable adhesive when the article is in use.

11. The absorbent article of claim 10 wherein the thermally activatable adhesive is disposed in the first waist region and the adhesive receiving zone is disposed in the second waist region.

12. The absorbent article of claim 1 further comprising a side panel, wherein the thermally activatable adhesive is disposed on the side panel.

13. The absorbent article of claim 12 wherein the side panel is disposed in the first waist region or the second waist region.

14. The absorbent article of claim 1 further comprises a fastening system.

15. The absorbent article of claim 14 wherein the fastening system includes the thermally activatable adhesive.

16. The absorbent article of claim 15 wherein the fastening system is configured to join said first waist region to said second waist region when the article is configured for use.

17. The absorbent article of claim 15 wherein the fastening system is configured so as to provide a disposal feature for the article.

18. The absorbent article of claim 1 wherein the thermally activatable adhesive is a topical adhesive.

19. The absorbent article of claim 1 wherein the thermally activatable adhesive has an pre-activation adhesion value and an activated adhesion value, the activated adhesion level being greater than the pre-activation adhesion value.

20. The absorbent article of claim 19 wherein the pre-activation adhesion is less than about 10 g/in.

21. The absorbent article of claim 19 wherein the pre-activation adhesion is between about 2 g/in and about 100 g/in.

22. The absorbent article of claim 19 wherein the pre-activation adhesion is between about 5 g/in and about 50 g/in.

23. The absorbent article of claim 19 wherein the activated adhesion is at least about twice the pre-activated adhesion.

24. The absorbent article of claim 19 wherein the activated adhesion is at least about five times the pre-activated adhesion.

25. The absorbent article of claim 19 wherein the activated adhesion value is one hundred times the pre-activation adhesion value.

26. The absorbent article of claim 19 wherein the activated adhesion value is between about 25 g/in and about 700 g/in.

27. The absorbent article of claim 1 wherein the thermally activatable adhesive has an activation temperature of between about 28° C. and about 60° C.

28. The absorbent article of claim 1 wherein the thermally activatable adhesive has an activation temperature of between about 30° C. and about 40° C.

29. The absorbent article of claim 1 wherein the heat source is reusable.

30. The absorbent article of claim 1 wherein the heat source generates heat by means of one or more of the following: exothermic chemical reaction, formation of a solution having a positive heat of solution, oxidative chemical reaction, resistive heating, thermoelectric effects and a latent heat of phase change.

31. The absorbent article of claim 1 wherein the heat source includes one or more of the following: liquid, particles, gel, fibers and foam.

32. The absorbent article of claim 1 wherein the heat source is removable from the article.

33. An absorbent article having a first waist region, a second waist region and a crotch region located between the first waist region and the second waist region, the absorbent article comprising:
- a topsheet,
- a backsheet joined with at least a portion of the topsheet,
- an absorbent core disposed between at least a portion of the topsheet and the backsheet,
- a thermally activatable adhesive disposed on at least a portion of the body-contacting surface of the article for adhering the surface of the absorbent article to the wearer during use, and
- a heat source to activate the adhesive.

34. The absorbent article of claim 33 wherein the heat source is reusable.

35. The absorbent article of claim 33 further including a primary aperture in the topsheet for receiving fecal waste.

36. The absorbent article of claim 35 wherein the thermally activatable adhesive is disposed about at least a portion of the primary aperture.

37. The absorbent article of claim 35 wherein the primary aperture has an area between about 10 cm$^2$ and about 50 cm$^2$.

38. The absorbent article of claim 35 wherein the primary aperture has an area between about 15 cm$^2$ and about 35 cm$^2$.

39. The absorbent article of claim 33 additionally comprising a spacing member disposed between the topsheet and the backsheet, the spacing member providing a void space into which feces can be directed.

40. The absorbent article of claim 39 wherein the spacing member is resilient.

41. The absorbent article of claim 39 wherein the spacing member has a void space volume of between about 10 and about 150 cm$^3$.

42. The absorbent article of claim 33 wherein the thermally activatable adhesive is a topical adhesive.

43. The absorbent article of claim 33 wherein the thermally activatable adhesive has an pre-activation adhesion value and an activated adhesion value, the activated adhesion level being greater than the pre-activation adhesion value.

44. The absorbent article of claim 43 wherein the pre-activation adhesion is less than about 10 g/in.

45. The absorbent article of claim 43 wherein the pre-activation adhesion is between about 2 g/in and about 100 g/in.

46. The absorbent article of claim 43 wherein the pre-activation adhesion is between about 5 g/in and about 50 g/in.

47. The absorbent article of claim 43 wherein the activated adhesion is at least about twice the pre-activated adhesion.

48. The absorbent article of claim 43 wherein the activated adhesion is at least about five times the pre-activated adhesion.

49. The absorbent article of claim 43 wherein the activated adhesion value is one hundred times the pre-activation adhesion value.

50. The absorbent article of claim 43 wherein the activated adhesion value is between about 25 g/in and about 700 g/in.

51. The absorbent article of claim 33 wherein the thermally activatable adhesive has an activation temperature of between about 28° C. and about 60° C.

52. The absorbent article of claim 33 wherein the thermally activatable adhesive has an activation temperature of between about 30° C. and about 40° C.

53. The absorbent article of claim 33 wherein the heat source is removable from the article.

54. The absorbent article of claim 33 wherein the heat source generates heat by means of one or more of the following: exothermic chemical reaction, formation of a solution having a positive heat of solution, resistive heating, oxidative chemical reaction, thermoelectric effects and a latent heat of phase change.

55. The absorbent article of claim 33 wherein the heat source includes one or more of the following: liquid, gel, particles, fibers and foam.

56. A feminine hygiene article comprising:
- a topsheet,
- a backsheet,
- an absorbent core disposed between the topsheet and the backsheet;
- a thermally activatable adhesive disposed on at least a portion of the article, and
- a heat source to activate the adhesive.

57. The feminine hygiene article of claim 56 wherein the heat source generates heat by means of one or more of the following: exothermic chemical reaction, formation of a solution having a positive heat of solution, resistive heating, oxidative chemical reaction, thermoelectric effects and a latent heat of phase change.

58. The feminine hygiene of claim 56 wherein the thermally activatable adhesive has a pre-activation adhesion value and an activated adhesion value, the activated adhesion level being greater than the pre-activation adhesion value.

59. The feminine hygiene article of claim 56 wherein the thermally activatable adhesive is disposed on at least a portion of the topsheet or backsheet of the article.

60. The feminine hygiene article of claim 56 further including at least one wing extending laterally outwardly from the absorbent care, wherein the thermally activatable adhesive is disposed on at least a portion of the wing.

* * * * *

UNITED STATES PATENT AND TRADEMARK OFFICE
CERTIFICATE OF CORRECTION

PATENT NO. : 6,565,549 B1
DATED : May 20, 2003
INVENTOR(S) : Allen et al.

It is certified that error appears in the above-identified patent and that said Letters Patent is hereby corrected as shown below:

Column 26,
Line 64, please delete "care" and insert therefor -- core --.

Signed and Sealed this

Tenth Day of August, 2004

JON W. DUDAS
*Acting Director of the United States Patent and Trademark Office*